US011154422B2

(12) United States Patent
Ross et al.

(10) Patent No.: US 11,154,422 B2
(45) Date of Patent: Oct. 26, 2021

(54) SURGICAL CASSETTE MANIFOLD, SYSTEM, AND METHODS THEREOF

(71) Applicant: JOHNSON & JOHNSON SURGICAL VISION, INC., Santa Ana, CA (US)

(72) Inventors: Mark W. Ross, Costa Mesa, CA (US); James B. Gerg, Lake Forest, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 351 days.

(21) Appl. No.: 16/291,582

(22) Filed: Mar. 4, 2019

(65) Prior Publication Data

US 2019/0201239 A1    Jul. 4, 2019

Related U.S. Application Data

(60) Division of application No. 14/686,582, filed on Apr. 14, 2015, now Pat. No. 10,219,938, which is a
(Continued)

(51) Int. Cl.
*A61F 9/00*  (2006.01)
*A61F 9/007*  (2006.01)
(Continued)

(52) U.S. Cl.
CPC .......... *A61F 9/00736* (2013.01); *A47B 81/00* (2013.01); *A61B 3/16* (2013.01);
(Continued)

(58) Field of Classification Search
CPC ... A61F 9/007; A61F 9/00736; A61M 1/0025; A61M 1/0058; A61M 2205/12;
(Continued)

(56) References Cited

U.S. PATENT DOCUMENTS 1,848,024 A    3/1932    Owen
2,123,781 A    7/1938    Huber
(Continued)

FOREIGN PATENT DOCUMENTS

AU    2006235983 A1    5/2007
DE       3826414 A1    2/1989
(Continued)

OTHER PUBLICATIONS

Boyd, "Preparing for the Transition" in: The Art and the Science of Cataract Surgery, Chapter 7, 2001, pp. 93-133.
(Continued)

*Primary Examiner* — Rebecca E Eisenberg
(74) *Attorney, Agent, or Firm* — Johnson & Johnson Surgical Vision, Inc.

(57) ABSTRACT

Eliminating leaks of molded fluid channels by providing a front housing, rear housing, and a gasket, wherein the front housing has one or more molded fluid channels and one or more seal channels, and wherein at least a portion of the gasket is located between the front and rear housing; molding the gasket onto the rear housing to create a single unit, wherein the gasket has one or more seal lips configured and dimensioned to couple with the one or more seal channels; and assembling the front housing to the rear housing having the gasket, wherein the one or more seal lips couple with the seal channels. A surgical cassette manifold having a front and rear housing, and a gasket therebetween. The front housing having molded fluid channels that mate with the gasket and the gasket having multiple valves and a sensor/diaphragm accessible through the rear housing.

3 Claims, 11 Drawing Sheets

Related U.S. Application Data continuation-in-part of application No. 13/776,988, filed on Feb. 26, 2013, now Pat. No. 9,700,457.

(60) Provisional application No. 61/612,307, filed on Mar. 17, 2012.

(51) Int. Cl.
| | |
|---|---|
| *A61F 9/008* | (2006.01) |
| *A61M 1/00* | (2006.01) |
| *A61M 3/02* | (2006.01) |
| *A61B 3/16* | (2006.01) |
| *A47B 81/00* | (2006.01) |

(52) U.S. Cl.
CPC .............. *A61F 9/007* (2013.01); *A61F 9/008* (2013.01); *A61F 9/00745* (2013.01); *A61M 1/0023* (2013.01); *A61M 1/0058* (2013.01); *A61M 3/022* (2014.02); *A61M 3/0216* (2014.02); *A61M 1/73* (2021.05); *A61M 3/0258* (2013.01); *A61M 2205/12* (2013.01); *A61M 2205/121* (2013.01); *A61M 2205/123* (2013.01); *A61M 2205/128* (2013.01); *A61M 2205/3331* (2013.01); *A61M 2205/3379* (2013.01); *A61M 2205/505* (2013.01); *A61M 2210/0612* (2013.01); *Y10T 29/49826* (2015.01)

(58) Field of Classification Search
CPC ...... A61M 2205/121; A61M 2205/123; A61M 2205/128; A61M 2205/3379; A61M 3/0258

See application file for complete search history.

(56) References Cited

U.S. PATENT DOCUMENTS

| | | | |
|---|---|---|---|
| 2,990,616 A | 7/1961 | Balamuth et al. |
| 3,076,904 A | 2/1963 | Claus et al. |
| 3,116,697 A | 1/1964 | Theodore |
| 3,439,680 A | 4/1969 | Thomas, Jr. |
| 3,526,219 A | 9/1970 | Lewis |
| 3,781,142 A | 12/1973 | Zweig |
| 3,857,387 A | 12/1974 | Shock |
| 4,017,828 A | 4/1977 | Watanabe et al. |
| 4,037,491 A | 7/1977 | Newbold |
| 4,189,286 A | 2/1980 | Murry et al. |
| 4,193,004 A | 3/1980 | Lobdell et al. |
| 4,247,784 A | 1/1981 | Henry |
| 4,276,023 A | 6/1981 | Phillips et al. |
| 4,286,464 A | 9/1981 | Tauber et al. |
| 4,479,760 A | 10/1984 | Bilstad et al. |
| 4,537,561 A | 8/1985 | Xanthopoulos |
| 4,564,342 A | 1/1986 | Weber et al. |
| 4,590,934 A | 5/1986 | Malis et al. |
| 4,662,829 A | 5/1987 | Nehring |
| 4,665,621 A | 5/1987 | Ackerman et al. |
| 4,706,687 A | 11/1987 | Rogers et al. |
| 4,713,051 A | 12/1987 | Steppe et al. |
| 4,757,814 A | 7/1988 | Wang et al. |
| 4,758,220 A | 7/1988 | Sundblom et al. |
| 4,758,238 A | 7/1988 | Sundblom et al. |
| 4,772,263 A | 9/1988 | Dorman et al. |
| 4,773,897 A | 9/1988 | Scheller et al. |
| 4,818,186 A | 4/1989 | Pastrone et al. |
| 4,819,317 A | 4/1989 | Bauer et al. |
| 4,837,857 A | 6/1989 | Scheller et al. |
| 4,920,336 A | 4/1990 | Meijer |
| 4,921,477 A | 5/1990 | Davis |
| 4,925,444 A | 5/1990 | Orkin et al. |
| 4,933,843 A | 6/1990 | Scheller et al. |
| 4,941,518 A | 7/1990 | Williams et al. |
| 4,954,960 A | 9/1990 | Lo et al. |
| 4,961,424 A | 10/1990 | Kubota et al. |
| 4,965,417 A | 10/1990 | Massie |
| 4,983,901 A | 1/1991 | Lehmer |
| 4,998,972 A | 3/1991 | Chin et al. |
| 5,006,110 A | 4/1991 | Garrison et al. |
| 5,020,535 A | 6/1991 | Parker et al. |
| 5,026,387 A | 6/1991 | Thomas |
| 5,032,939 A | 7/1991 | Mihara et al. |
| 5,039,973 A | 8/1991 | Carballo |
| 5,091,656 A | 2/1992 | Gahn |
| 5,108,367 A | 4/1992 | Epstein et al. |
| 5,110,270 A | 5/1992 | Morrick |
| 5,125,891 A | 6/1992 | Hossain et al. |
| 5,160,317 A | 11/1992 | Costin |
| 5,195,960 A | 3/1993 | Hossain et al. |
| 5,195,961 A | 3/1993 | Takahashi et al. |
| 5,195,971 A | 3/1993 | Sirhan |
| 5,230,614 A | 7/1993 | Zanger et al. |
| 5,242,404 A | 9/1993 | Conley et al. |
| 5,249,121 A | 9/1993 | Baum et al. |
| 5,267,956 A | 12/1993 | Beuchat |
| 5,268,624 A | 12/1993 | Zanger |
| 5,271,379 A | 12/1993 | Phan et al. |
| 5,273,517 A | 12/1993 | Barone et al. |
| 5,282,787 A | 2/1994 | Wortrich |
| 5,323,543 A | 6/1994 | Steen et al. |
| 5,342,293 A | 8/1994 | Zanger |
| 5,350,357 A | 9/1994 | Kamen et al. |
| 5,351,676 A | 10/1994 | Putman |
| 5,354,268 A | 10/1994 | Peterson et al. |
| 5,378,126 A | 1/1995 | Abrahamson et al. |
| 5,388,569 A | 2/1995 | Kepley |
| 5,429,601 A | 7/1995 | Conley et al. |
| 5,445,506 A | 8/1995 | Afflerbaugh et al. |
| 5,454,783 A | 10/1995 | Grieshaber et al. |
| 5,464,391 A | 11/1995 | Devale |
| 5,470,211 A | 11/1995 | Knott et al. |
| 5,470,312 A | 11/1995 | Zanger et al. |
| 5,499,969 A | 3/1996 | Beuchat et al. |
| 5,520,652 A | 5/1996 | Peterson |
| 5,533,976 A | 7/1996 | Zaleski et al. |
| 5,549,461 A | 8/1996 | Newland |
| 5,554,894 A | 9/1996 | Sepielli |
| 5,561,575 A | 10/1996 | Eways |
| 5,569,188 A | 10/1996 | Mackool |
| 5,580,347 A | 12/1996 | Reimels |
| 5,591,127 A | 1/1997 | Barwick et al. |
| 5,653,887 A | 8/1997 | Wahl et al. |
| 5,657,000 A | 8/1997 | Ellingboe |
| 5,676,530 A | 10/1997 | Nazarifar |
| 5,676,649 A | 10/1997 | Boukhny et al. |
| 5,676,650 A | 10/1997 | Grieshaber et al. |
| 5,693,020 A | 12/1997 | Rauh |
| 5,697,898 A | 12/1997 | Devine |
| 5,697,910 A | 12/1997 | Cole et al. |
| 5,700,240 A | 12/1997 | Barwick, Jr. et al. |
| 5,724,264 A | 3/1998 | Rosenberg et al. |
| 5,728,130 A | 3/1998 | Ishikawa et al. |
| 5,733,256 A | 3/1998 | Costin |
| 5,733,263 A | 3/1998 | Wheatman |
| 5,745,647 A | 4/1998 | Krause |
| 5,746,713 A | 5/1998 | Hood et al. |
| 5,747,824 A | 5/1998 | Jung et al. |
| 5,752,918 A | 5/1998 | Fowler et al. |
| 5,777,602 A | 7/1998 | Schaller et al. |
| 5,805,998 A | 9/1998 | Kodama |
| 5,807,075 A | 9/1998 | Jacobsen et al. |
| 5,810,765 A | 9/1998 | Oda |
| 5,810,766 A | 9/1998 | Barnitz et al. |
| 5,830,176 A | 11/1998 | Mackool |
| 5,843,109 A | 12/1998 | Mehta et al. |
| 5,859,642 A | 1/1999 | Jones |
| 5,871,492 A | 2/1999 | Sorensen |
| 5,879,298 A | 3/1999 | Drobnitzky et al. |
| 5,883,615 A | 3/1999 | Fago et al. |
| 5,899,674 A | 5/1999 | Jung et al. |
| 5,928,257 A | 7/1999 | Kablik et al. |
| 5,938,655 A | 8/1999 | Bisch et al. |
| 5,983,749 A | 11/1999 | Holtorf |

(56) References Cited

U.S. PATENT DOCUMENTS

| | | |
|---|---|---|
| 6,002,484 A | 12/1999 | Rozema et al. |
| 6,024,428 A | 2/2000 | Uchikata |
| 6,028,387 A | 2/2000 | Boukhny |
| 6,062,829 A | 5/2000 | Ognier |
| 6,077,285 A | 6/2000 | Boukhny |
| 6,086,598 A | 7/2000 | Appelbaum et al. |
| 6,109,895 A | 8/2000 | Ray et al. |
| 6,117,126 A | 9/2000 | Appelbaum et al. |
| 6,139,320 A | 10/2000 | Hahn |
| 6,150,623 A | 11/2000 | Chen |
| 6,159,175 A | 12/2000 | Strukel et al. |
| 6,179,829 B1 | 1/2001 | Bisch et al. |
| 6,200,287 B1 | 3/2001 | Keller et al. |
| 6,219,032 B1 | 4/2001 | Rosenberg et al. |
| 6,251,113 B1 | 6/2001 | Appelbaum et al. |
| 6,260,434 B1 | 7/2001 | Holtorf |
| 6,360,630 B2 | 3/2002 | Holtorf |
| 6,368,269 B1 | 4/2002 | Lane |
| 6,383,804 B1 | 5/2002 | Ward, Jr. et al. |
| 6,411,062 B1 | 6/2002 | Baranowski et al. |
| 6,424,124 B2 | 7/2002 | Ichihara et al. |
| 6,436,072 B1 | 8/2002 | Kullas et al. |
| 6,452,120 B1 | 9/2002 | Chen |
| 6,452,123 B1 | 9/2002 | Chen |
| 6,491,661 B1 | 12/2002 | Boukhny et al. |
| 6,511,454 B1 | 1/2003 | Nakao et al. |
| 6,537,445 B2 | 3/2003 | Muller |
| 6,561,999 B1 | 5/2003 | Nazarifar et al. |
| 6,595,948 B2 | 7/2003 | Suzuki et al. |
| 6,595,957 B1* | 7/2003 | Griffiths .............. A61M 3/0258 604/156 |
| 6,632,214 B2 | 10/2003 | Morgan et al. |
| 6,674,030 B2 | 1/2004 | Chen et al. |
| 6,830,555 B2 | 12/2004 | Rockley et al. |
| 6,852,092 B2 | 2/2005 | Kadziauskas et al. |
| 6,862,951 B2 | 3/2005 | Peterson et al. |
| 6,908,451 B2 | 6/2005 | Brody et al. |
| 6,962,488 B2 | 11/2005 | Davis et al. |
| 6,962,581 B2 | 11/2005 | Thoe |
| 6,986,753 B2 | 1/2006 | Bui |
| 7,011,761 B2 | 3/2006 | Muller |
| 7,012,203 B2 | 3/2006 | Hanson et al. |
| 7,070,578 B2 | 7/2006 | Leukanech et al. |
| 7,073,083 B2 | 7/2006 | Litwin, Jr. et al. |
| 7,087,049 B2 | 8/2006 | Nowlin et al. |
| 7,103,344 B2 | 9/2006 | Menard |
| 7,167,723 B2 | 1/2007 | Zhang |
| 7,169,123 B2 | 1/2007 | Kadziauskas et al. |
| 7,236,766 B2 | 6/2007 | Freeburg |
| 7,236,809 B2 | 6/2007 | Fischedick et al. |
| 7,242,765 B2 | 7/2007 | Hairston |
| 7,244,240 B2 | 7/2007 | Nazarifar et al. |
| 7,289,825 B2 | 10/2007 | Fors et al. |
| 7,300,264 B2 | 11/2007 | Souza |
| 7,316,664 B2 | 1/2008 | Kadziauskas et al. |
| 7,336,976 B2 | 2/2008 | Ito |
| 7,381,917 B2 | 6/2008 | Dacquay et al. |
| 7,439,463 B2 | 10/2008 | Brenner et al. |
| 7,465,285 B2 | 12/2008 | Hutchinson et al. |
| 7,470,277 B2 | 12/2008 | Finlay et al. |
| 7,526,038 B2 | 4/2009 | McNamara |
| 7,591,639 B2 | 9/2009 | Kent |
| 7,731,484 B2 | 6/2010 | Yamamoto et al. |
| 7,776,006 B2 | 8/2010 | Childers et al. |
| 7,785,316 B2 | 8/2010 | Claus et al. |
| 7,811,255 B2 | 10/2010 | Boukhny et al. |
| 7,883,521 B2 | 2/2011 | Rockley et al. |
| 7,921,017 B2 | 4/2011 | Claus et al. |
| 7,967,777 B2 | 6/2011 | Edwards et al. |
| 8,070,712 B2 | 12/2011 | Muri et al. |
| 8,075,468 B2 | 12/2011 | Min et al. |
| 9,033,940 B2 | 5/2015 | Muri et al. |
| 2001/0015227 A1 | 8/2001 | Jorgensen et al. |
| 2001/0023331 A1 | 9/2001 | Kanda et al. |
| 2001/0047166 A1 | 11/2001 | Wuchinich |
| 2001/0051788 A1 | 12/2001 | Paukovits et al. |
| 2002/0004657 A1 | 1/2002 | Morgan et al. |
| 2002/0007671 A1 | 1/2002 | Lavi et al. |
| 2002/0019215 A1 | 2/2002 | Romans |
| 2002/0045887 A1 | 4/2002 | Dehoogh et al. |
| 2002/0070840 A1 | 6/2002 | Fischer et al. |
| 2002/0098859 A1 | 7/2002 | Murata |
| 2002/0137007 A1 | 9/2002 | Beerstecher |
| 2002/0179462 A1 | 12/2002 | Silvers |
| 2002/0183693 A1 | 12/2002 | Peterson et al. |
| 2003/0028091 A1 | 2/2003 | Simon et al. |
| 2003/0050619 A1 | 3/2003 | Mooijman et al. |
| 2003/0083016 A1 | 5/2003 | Evans et al. |
| 2003/0108429 A1 | 6/2003 | Angelini et al. |
| 2003/0125717 A1 | 7/2003 | Whitman |
| 2003/0190244 A1 | 10/2003 | Davis et al. |
| 2003/0224729 A1 | 12/2003 | Arnold |
| 2003/0226091 A1 | 12/2003 | Platenberg et al. |
| 2004/0019313 A1 | 1/2004 | Childers et al. |
| 2004/0037724 A1 | 2/2004 | Haser et al. |
| 2004/0097868 A1 | 5/2004 | Kadziauskas et al. |
| 2004/0127840 A1 | 7/2004 | Gara et al. |
| 2004/0193182 A1 | 9/2004 | Yaguchi et al. |
| 2004/0212344 A1 | 10/2004 | Tamura et al. |
| 2004/0215127 A1 | 10/2004 | Kadziauskas et al. |
| 2004/0224641 A1 | 11/2004 | Sinn |
| 2004/0253129 A1 | 12/2004 | Sorensen et al. |
| 2005/0039567 A1 | 2/2005 | Peterson et al. |
| 2005/0054971 A1 | 3/2005 | Steen et al. |
| 2005/0069419 A1 | 3/2005 | Cull et al. |
| 2005/0070859 A1 | 3/2005 | Cull et al. |
| 2005/0070871 A1 | 3/2005 | Lawton et al. |
| 2005/0095153 A1 | 5/2005 | Demers et al. |
| 2005/0103607 A1 | 5/2005 | Mezhinsky |
| 2005/0109595 A1 | 5/2005 | Mezhinsky et al. |
| 2005/0118048 A1 | 6/2005 | Traxinger |
| 2005/0119679 A1 | 6/2005 | Rabiner et al. |
| 2005/0130098 A1 | 6/2005 | Warner |
| 2005/0187513 A1 | 8/2005 | Rabiner et al. |
| 2005/0197131 A1 | 9/2005 | Ikegami |
| 2005/0209552 A1 | 9/2005 | Beck et al. |
| 2005/0228266 A1 | 10/2005 | McCombs |
| 2005/0236936 A1 | 10/2005 | Shiv et al. |
| 2005/0245888 A1 | 11/2005 | Cull |
| 2005/0261628 A1 | 11/2005 | Boukhny et al. |
| 2005/0267504 A1 | 12/2005 | Boukhny et al. |
| 2006/0035585 A1 | 2/2006 | Washiro |
| 2006/0036180 A1 | 2/2006 | Boukhny et al. |
| 2006/0041220 A1 | 2/2006 | Boukhny et al. |
| 2006/0046659 A1 | 3/2006 | Haartsen et al. |
| 2006/0074405 A1 | 4/2006 | Malackowski et al. |
| 2006/0078448 A1 | 4/2006 | Holden |
| 2006/0114175 A1 | 6/2006 | Boukhny |
| 2006/0145540 A1 | 7/2006 | Mezhinsky |
| 2006/0219049 A1 | 10/2006 | Horvath et al. |
| 2006/0219962 A1 | 10/2006 | Dancs et al. |
| 2006/0224107 A1 | 10/2006 | Claus et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0073214 A1 | 3/2007 | Dacquay et al. |
| 2007/0073309 A1 | 3/2007 | Kadziauskas et al. |
| 2007/0078379 A1 | 4/2007 | Boukhny et al. |
| 2007/0085611 A1 | 4/2007 | Gerry et al. |
| 2007/0107490 A1 | 5/2007 | Artsyukhovich et al. |
| 2007/0231205 A1 | 10/2007 | Williams et al. |
| 2007/0232990 A1* | 10/2007 | Hopkins ................ G01F 1/663 604/30 |
| 2007/0249942 A1 | 10/2007 | Salehi et al. |
| 2007/0287959 A1 | 12/2007 | Walter et al. |
| 2008/0033342 A1 | 2/2008 | Staggs |
| 2008/0066542 A1 | 3/2008 | Gao |
| 2008/0082040 A1 | 4/2008 | Kubler et al. |
| 2008/0112828 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |

(56) References Cited

U.S. PATENT DOCUMENTS

| | | |
|---|---|---|
| 2008/0114312 A1 | 5/2008 | Muri et al. |
| 2008/0114387 A1 | 5/2008 | Hertweck et al. |
| 2008/0125694 A1 | 5/2008 | Domash |
| 2008/0125695 A1 | 5/2008 | Hopkins et al. |
| 2008/0125697 A1 | 5/2008 | Gao |
| 2008/0125698 A1 | 5/2008 | Gerg et al. |
| 2008/0129695 A1 | 6/2008 | Li |
| 2008/0146989 A1 | 6/2008 | Zacharias |
| 2008/0200878 A1 | 8/2008 | Davis et al. |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2008/0312594 A1 | 12/2008 | Urich et al. |
| 2009/0005712 A1 | 1/2009 | Raney |
| 2009/0005789 A1 | 1/2009 | Charles |
| 2009/0048607 A1 | 2/2009 | Rockley |
| 2009/0087327 A1 | 4/2009 | Voltenburg, Jr. et al. |
| 2009/0124974 A1 | 5/2009 | Crank et al. |
| 2009/0163853 A1 | 6/2009 | Cull et al. |
| 2010/0036256 A1 | 2/2010 | Boukhny et al. |
| 2010/0057016 A1 | 3/2010 | Dale et al. |
| 2010/0069825 A1 | 3/2010 | Raney |
| 2010/0069828 A1 | 3/2010 | Steen et al. |
| 2010/0140149 A1 | 6/2010 | Fulkerson et al. |
| 2010/0152685 A1 | 6/2010 | Goh |
| 2010/0185150 A1 | 7/2010 | Zacharias |
| 2010/0249693 A1 | 9/2010 | Links |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |
| 2011/0208047 A1 | 8/2011 | Fago |
| 2011/0251569 A1 | 10/2011 | Turner et al. |
| 2011/0300010 A1 | 12/2011 | Jarnagin et al. |
| 2012/0065580 A1 | 3/2012 | Gerg et al. |
| 2012/0078181 A1 | 3/2012 | Smith et al. |
| 2012/0083735 A1 | 4/2012 | Pfouts |
| 2012/0083736 A1 | 4/2012 | Pfouts et al. |
| 2012/0083800 A1 | 4/2012 | Andersohn et al. |
| 2013/0072853 A1 | 3/2013 | Wong et al. |
| 2013/0169412 A1 | 7/2013 | Roth |
| 2013/0184676 A1 | 7/2013 | Kamen et al. |
| 2013/0245543 A1 | 9/2013 | Gerg et al. |
| 2013/0267892 A1 | 10/2013 | Woolford et al. |
| 2013/0289475 A1 | 10/2013 | Muri et al. |
| 2013/0303978 A1 | 11/2013 | Ross |
| 2013/0336814 A1 | 12/2013 | Kamen et al. |
| 2014/0178215 A1 | 6/2014 | Baxter et al. |
| 2014/0188076 A1 | 7/2014 | Kamen et al. |
| 2014/0276424 A1 | 9/2014 | Davis et al. |
| 2016/0151564 A1 | 6/2016 | Magers et al. |

FOREIGN PATENT DOCUMENTS

| | | |
|---|---|---|
| EP | 56019 A1 | 7/1982 |
| EP | 424687 A1 | 5/1991 |
| EP | 0619993 A1 | 10/1994 |
| EP | 1010437 A1 | 6/2000 |
| EP | 1072285 A1 | 1/2001 |
| EP | 1113562 A1 | 7/2001 |
| EP | 1464310 A1 | 10/2004 |
| EP | 1469440 A2 | 10/2004 |
| EP | 1550406 A2 | 7/2005 |
| EP | 1704839 A1 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1310267 B1 | 1/2008 |
| EP | 1873501 A1 | 1/2008 |
| EP | 1900347 A1 | 3/2008 |
| EP | 1925274 A2 | 5/2008 |
| EP | 1867349 B1 | 11/2008 |
| ES | 2264369 A1 | 12/2006 |
| GB | 2230301 A | 10/1990 |
| GB | 2438679 A | 12/2007 |
| JP | S5724482 A | 2/1982 |
| JP | S58167333 A | 10/1983 |
| JP | S62204463 A | 9/1987 |
| JP | 2005195653 A | 7/2005 |
| JP | 2008188110 A | 8/2008 |
| WO | 9220310 A1 | 11/1992 |
| WO | 9315777 A2 | 8/1993 |
| WO | 9317729 A1 | 9/1993 |
| WO | 9324082 A1 | 12/1993 |
| WO | 9405346 A1 | 3/1994 |
| WO | 9632144 A1 | 10/1996 |
| WO | 9737700 A1 | 10/1997 |
| WO | 9818507 A1 | 5/1998 |
| WO | 9917818 A1 | 4/1999 |
| WO | 0000096 A1 | 1/2000 |
| WO | 0070225 A1 | 11/2000 |
| WO | 0226286 A2 | 4/2002 |
| WO | 0228449 A2 | 4/2002 |
| WO | 0234314 A1 | 5/2002 |
| WO | 03102878 A1 | 12/2003 |
| WO | 2004114180 A1 | 12/2004 |
| WO | 05084728 A2 | 9/2005 |
| WO | 05092023 A2 | 10/2005 |
| WO | 05092047 A2 | 10/2005 |
| WO | 06101908 A2 | 9/2006 |
| WO | 06125280 A1 | 11/2006 |
| WO | 2007121144 A1 | 10/2007 |
| WO | 2007143677 A2 | 12/2007 |
| WO | 2007143797 A1 | 12/2007 |
| WO | 2007149637 A2 | 12/2007 |
| WO | 2008030872 A1 | 3/2008 |
| WO | 2008060859 A1 | 5/2008 |
| WO | 2008060902 A1 | 5/2008 |
| WO | 2008060995 A1 | 5/2008 |
| WO | 2009123547 A1 | 10/2009 |
| WO | 2010054146 A1 | 5/2010 |
| WO | 2010054225 A2 | 5/2010 |
| WO | 2010151704 A1 | 12/2010 |
| WO | 2012006425 A2 | 1/2012 |
| WO | 2012151062 A1 | 11/2012 |
| WO | 2013142009 A1 | 9/2013 |
| WO | 2015009945 A1 | 1/2015 |

OTHER PUBLICATIONS

Definition of "Parameter", Retrieved from the Internet: URL: http://dictionary.reference.com/browse/parameter, Retrieved on Aug. 9, 2016.

Merritt R., et al., Wireless Nets Starting to link Medical Gear [online] 2004 [retrieved on Feb. 12, 2007]. Retrieved from the Internet: (http://www.embedded.com/news/embeddedindustry/17200577?_requestid=174370).

Phacoemulsification, [online] [retrieved on Jul. 1, 2009]. Retrieved from the Internet: , 2 pages.

\* cited by examiner

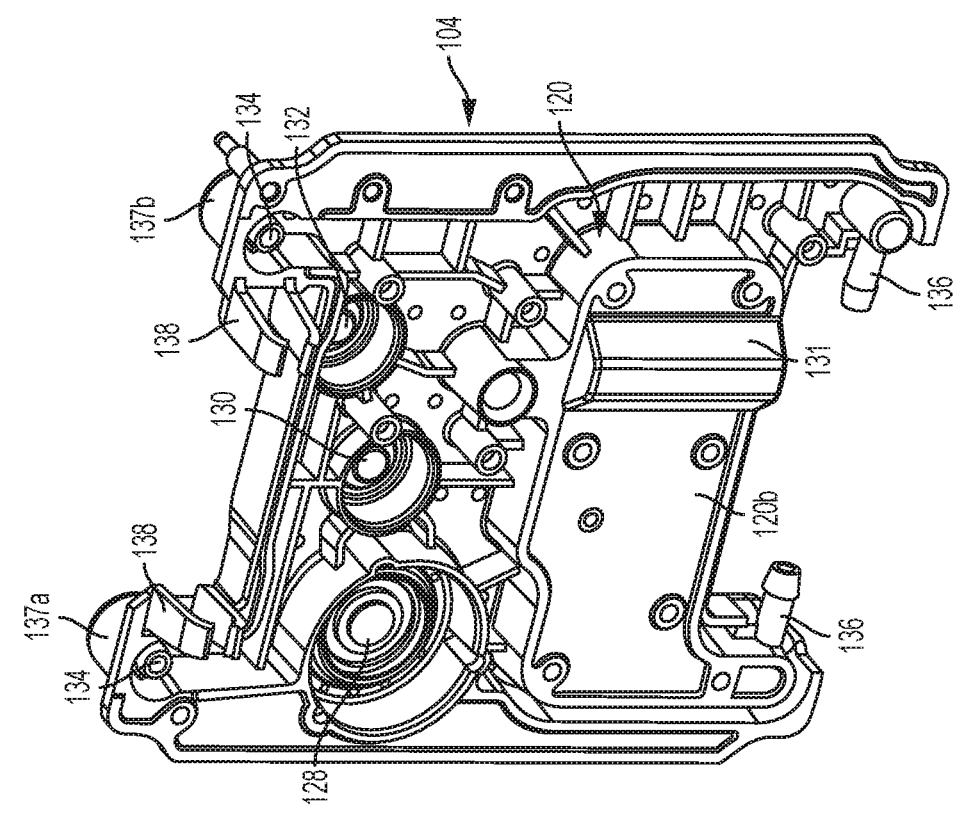

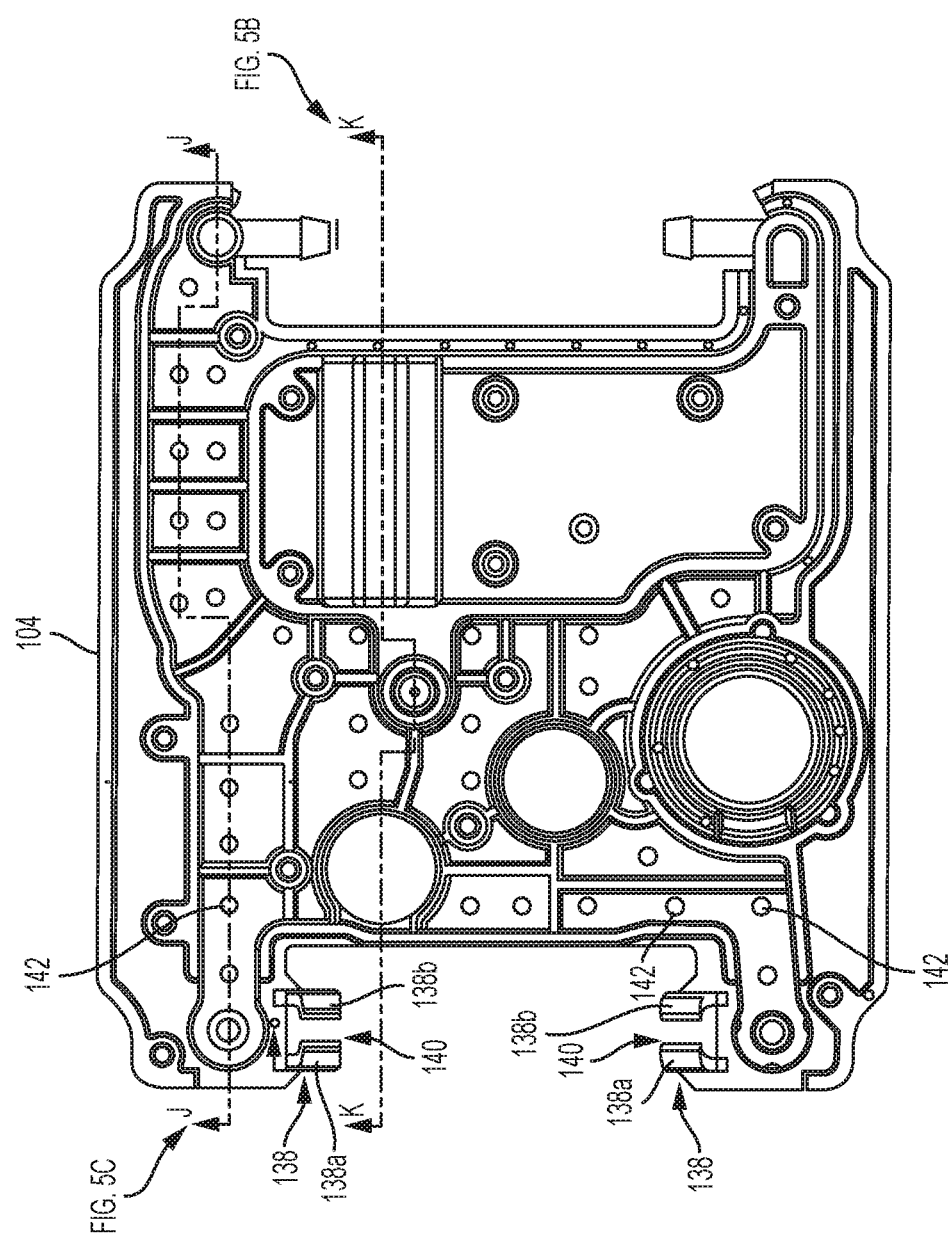

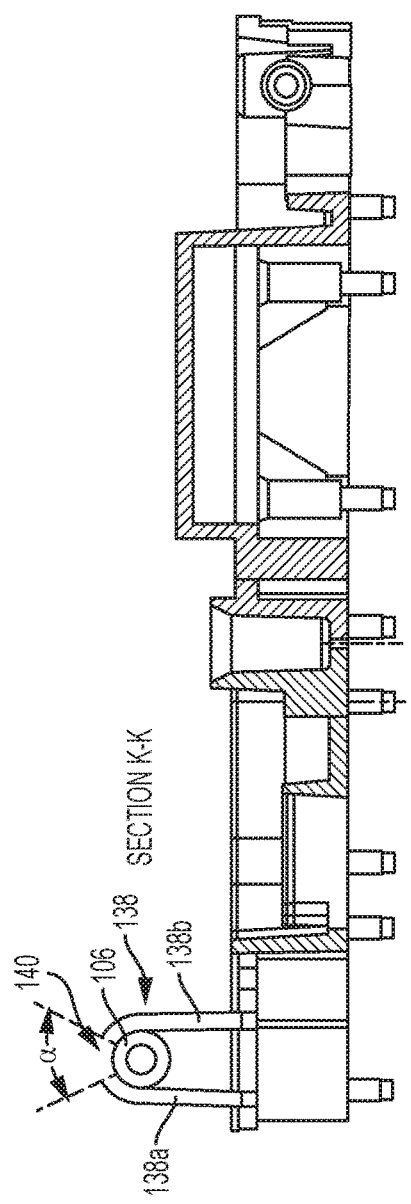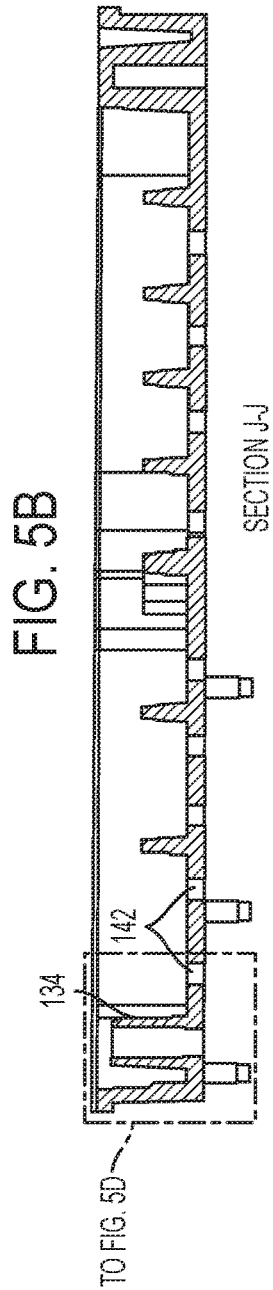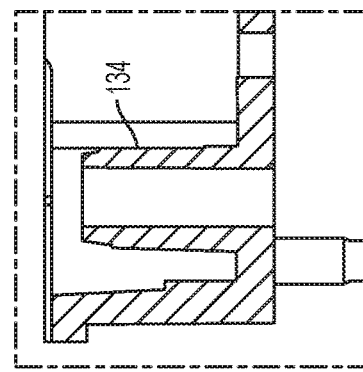
FIG. 5B
FIG. 5C
FIG. 5D

SURGICAL CASSETTE MANIFOLD, SYSTEM, AND METHODS THEREOF

CROSS-REFERENCE TO RELATED APPLICATIONS

This application claims priority to and is a divisional of U.S. patent application Ser. No. 14/686,582, filed Apr. 14, 2015, now U.S. Pat. No. 10,219,938, which claims priority to and is a continuation-in-part application of U.S. application Ser. No. 13/776,988 filed on Feb. 26, 2013, now U.S. Pat. No. 9,700,457, which claims priority to U.S. provisional application No. 61/612,307 filed on Mar. 17, 2012, the contents of each are hereby incorporated by reference in their entirety.

TECHNICAL FIELD OF THE INVENTION

The present invention is generally related to methods, devices, and systems for controlling surgical fluid flows, particularly during treatment of an eye.

BACKGROUND OF THE INVENTION

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil, and within a capsular bag. This capsular bag is a thin, relatively delicate structure which separates the eye into anterior and posterior chambers.

With age, clouding of the lens or cataracts are fairly common. Cataracts may form in the hard central nucleus of the lens, in the softer peripheral cortical portion of the lens, or at the back of the lens near the capsular bag.

Cataracts can be treated by the replacement of the cloudy lens with an artificial lens. Phacoemulsification systems often use ultrasound energy to fragment the lens and aspirate the lens material from within the capsular bag. This may allow the capsular bag to be used for positioning of the artificial lens, and maintains the separation between the anterior portion of the eye and the vitreous humour in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms have been used in phacoemulsification and other treatment systems for the eyes, aspiration flow systems can generally be classified in two categories: 1) volumetric-based aspiration flow systems using positive displacement pumps; and 2) vacuum-based aspiration systems using a vacuum source, typically applied to the aspiration flow through an air-liquid interface. These two categories of aspiration flow systems each have unique characteristics that render one more suitable for some procedures than the other, and vice versa.

Among positive displacement aspiration systems, peristaltic pumps (which use rotating rollers that press against a flexible tubing to induce flow) are commonly employed. Such pumps provide accurate control over the flow volume. The pressure of the flow, however, is less accurately controlled and the variations in vacuum may result in the feel or traction of the handpiece varying during a procedure. Peristaltic and other displacement pump systems may also be somewhat slow.

Vacuum-based aspiration systems provide accurate control over the fluid pressure within the eye, particularly when combined with gravity-fed irrigation systems. While vacuum-based systems can result in excessive fluid flows in some circumstances, they provide advantages, for example, when removing a relatively large quantity of the viscous vitreous humour from the posterior chamber of the eye. However, Venturi pumps and other vacuum-based aspiration flow systems are subject to pressure surges during occlusion of the treatment probe, and such pressure surges may decrease the surgeon's control over the eye treatment procedure.

Different tissues may be aspirated from the anterior chamber of the eye with the two different types of aspiration flow. For example, vacuum-induced aspiration flow may quickly aspirate tissues at a significant distance from a delicate structure of the eye (such as the capsular bag), while tissues that are closer to the capsular bag are aspirated more methodically using displacement-induced flows.

Conventionally, fluid aspiration systems include a console and a fluidic cassette mounted on the console. The fluidic cassette is typically changed for each patient and cooperates with the console to provide fluid aspiration. Generally, a single type of cassette is used by a particular console, regardless of whether the procedure will require positive displacement aspiration, vacuum-based aspiration, or both. U.S. Pat. No. 8,070,712; U.S. Published Application 2008011431; and U.S. Published Application 20080114291 provide examples of cassettes currently used in the marketplace, the contents of each are herewith incorporated by reference in their entirety as if set forth herein. U.S. application Ser. No. 13/776,988 provides examples of cassettes, which is hereby incorporated by reference in its entirety as if set forth herein.

In light of the above, it would be advantageous to provide improved devices, systems, and methods for eye surgery.

SUMMARY OF THE INVENTION

The present invention provides a method of eliminating leaking of molded fluid channels, including: providing a front housing, rear housing, and a gasket, wherein the front housing has one or more molded fluid channels and one or more seal channels, and wherein at least a portion of the gasket is located between the front housing and the rear housing; molding the gasket onto the rear housing to create a single unit, wherein the gasket has one or more seal lips configured and dimensioned to couple with the one or more seal channels; and assembling the front housing to the rear housing having the gasket, wherein the one or more seal lips couple with the seal channels. The seal channels may be located on an outside perimeter of the molded fluid channels and the seal lip may be tapered. In addition, the one or more seal lips may extend substantially perpendicular from a surface of the gasket. The molded fluid channels may also be substantially perpendicular with a surface of the front housing and/or the seal channels may be substantially perpendicular with a surface of the front housing. In addition, the seal lips may be configured and dimensioned as pre-alignment structures enabling proper assembly with corresponding seal channels. The method may further include one or more alignment pins and corresponding pin holes, wherein after molding the gasket onto the rear housing to create a single unit, coupling the alignment pins with the corresponding pin holes. The method may also include, after assembling the front housing to the rear housing having the gasket, ultrasonically welding the front housing to the rear housing. In addition, the method may include, after assembling the front housing to the rear housing having the gasket, press fitting the front housing to the rear housing.

The present invention provides a surgical cassette manifold, having a front housing, a rear housing, and a gasket, wherein the front housing comprises one or more molded fluid channels and one or more seal channels, herein the gasket is coupled with the rear housing and at least a portion of the gasket is located between the front housing and the rear housing, and wherein the gasket has one or more seal lips configured and dimensioned to couple with the one or more seal channels. The surgical cassette manifold may further include a reservoir, wherein the reservoir has a first portion with a first circumferential edge located in the front housing, a second portion with a second circumferential edge located in the rear housing, and wherein at least a portion of the gasket is located between the first and second circumferential edge when the front housing and rear housing are assembled. In addition, upon assembly of the surgical cassette manifold, the gasket creates a mechanical seal between the first portion and the second portion of the reservoir. The seal channels may be located on an outside perimeter of the molded fluid channels and the seal lip is tapered. The one or more seal lips extend substantially perpendicular from a surface of the gasket. The molded fluid channels may be substantially perpendicular with a surface of the front housing and/or the seal channels may be substantially perpendicular with a surface of the front housing. The seal lips may be configured and dimensioned as pre-alignment structures enabling proper assembly with the seal channels. In addition, the rear housing may further include one or more alignment pins and the front housing further includes one or more corresponding pin holes, wherein the one or more alignment pins and one or more pin holes are configured and dimensioned to mate upon assembly of the front housing and rear housing.

The present invention provides a surgical cassette manifold, having a front housing and a rear housing, wherein, the rear housing has a first side and a second side, wherein the first side is configured and dimensioned to make contact with a surgical console, wherein the first side has one or more retainer clips, wherein the retainer clips have a first prong and a second prong, wherein the first and second prong extend substantially perpendicular from a plane of the rear housing and have an opening between the first and second prong configured and dimensioned to accept a flexible tubing and retain the flexible tubing once accepted through the opening. The first prong and the second prong may have a proximal end and a distal end, wherein the opening has a length between the distal ends that is smaller than the length between the proximal ends. The distal end of the first prong may have a first face and the distal end of the second prong has a second face, wherein the first and second face of the opening create an angle. The angle may be an acute angle and the angle may be between 30 degrees and 90 degrees.

The present invention provides a surgical cassette manifold, including a front housing, wherein the front housing has a first side, a second side, a top and a bottom, wherein the first side has a drain port having a connection configured and dimension to couple with a drain bag, wherein the drain port is located approximately equidistance from the top and the bottom of the first side, and wherein the drain port is recessed such that the drain port is substantially flush with a surface of the first side of the front housing, wherein the second side of the front housing has one or more molded fluid channels which are fluidly connected to the drain port and wherein the front housing has one or more seal channels; a rear housing having a gasket coupled thereto, wherein the gasket comprises one or more seal lips configured and dimensioned to couple with the one or more seal channels to seal the one or more molded fluid channels; and wherein the one or more molded fluid channels comprises a vertical molded channel and the gasket has a seal lip that is configured and dimensioned to mate with the vertical seal channel to seal the vertical molded channel, wherein a bottom of the vertical molded channel couples with a lower tube connection that is coupled with a peristaltic pump and a top of the vertical molded channel couples with the drain port. The surgical cassette manifold may also have a handle, wherein the handle is coupled with the first side of the front housing and extends outwardly from the first side, wherein the handle is located substantially in the middle of the front housing between the first and second sides and above a horizontal midline between the top and bottom. In addition, the front housing further may have a first pump ramp and a second pump ramp, wherein the second pump rump is located near the bottom and a curvature profile of the second pump ramp extends outwardly beyond a surface of the first side but not beyond the handle.

The present invention provides a surgical cassette manifold, including a front housing, a rear housing, a gasket, and a tubing segment, wherein the gasket is coupled with the rear housing, and wherein upon assembly of the surgical cassette manifold, at least a portion of the gasket is located between the front housing and the rear housing, wherein the rear housing has a first lower tube connection and a second lower tube connection, wherein the first lower tube connection is configured and dimensioned to couple with a first end of the tubing segment and the second lower tubing segment is configured and dimensioned to couple with a second end of the tubing segment thereby creating a first portion of a peristaltic pump, wherein the first lower tube connection and second lower tube connection have an in flow and out flow path on a same axis. The surgical cassette manifold may further include a reservoir and the peristaltic pump may be configured and dimensioned to drain fluid from the reservoir via the first and second lower tube connections and tubing segment.

The present invention provides a surgical system, including a cassette having a front housing, a rear housing, and a reservoir, wherein the front housing has one or more molded fluid channels, and wherein the front housing, rear housing, and reservoir are made of a transparent material; a console having a cassette receptacle configured and dimensioned to receive the cassette, wherein the cassette receptacle has a light, wherein when in operation, the light is configured to illuminate the cassette enabling visualization of fluid flow through the molded fluid channels and/or into the reservoir. In addition, the system may further include a cassette detector, wherein the cassette detector is configured to determine the pumping functionality of the cassette. The pumping functionality may be selected from the group consisting of peristaltic, Venturi, or both. The cassette detector may be a reflective object sensor, a photo interrupter sensor, ultrasonic, a laser distance sensor, a bar code sensor, or a pattern recognition sensor.

The present invention provides a surgical cassette manifold, including a reservoir, wherein the reservoir has a sump and a baffle, wherein a port for fluid outflow is located within the sump; a front housing, wherein the front housing has a first side and a second side, wherein the first side has one or more fluid channels and a first half of the reservoir; and a rear housing, wherein the rear housing has a first side and a second side, wherein the first side has a second half of the reservoir and a gasket molded to at least a portion of the first side, wherein the first half of the reservoir comprises a baffle located near a top of the reservoir; wherein the sump is configured and dimensioned to draw fluid to the port to reduce turbulence in the reservoir. The cassette may further include a fluid level window, wherein the baffle is configured and dimensioned to limit fluid contact with the fluid level window. The baffle may be angled toward the sump to direct fluid flow from the fluid channels to the port.

BRIEF DESCRIPTION OF THE DRAWINGS

The present invention is best understood with reference to the following detailed description of the invention and the drawings in which:

FIG. 4A is a front perspective view of the rear housing of an exemplary surgical cassette manifold;

FIG. 4B is a back perspective view of the rear housing of an exemplary surgical cassette manifold;

FIG. 5A is back view of the rear housing of an exemplary surgical cassette manifold;

FIG. 5B is a cross-sectional view of the rear housing along N-N of an exemplary surgical cassette manifold;

FIG. 5C is a cross-sectional view of the rear housing of an exemplary surgical cassette manifold;

FIG. 5D is a larger view of a portion of cross-sectional view of the rear housing of the exemplary surgical cassette manifold shown in FIG. 5C.

DETAILED DESCRIPTION OF THE INVENTION

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined by the appended claims.

Figure 1:
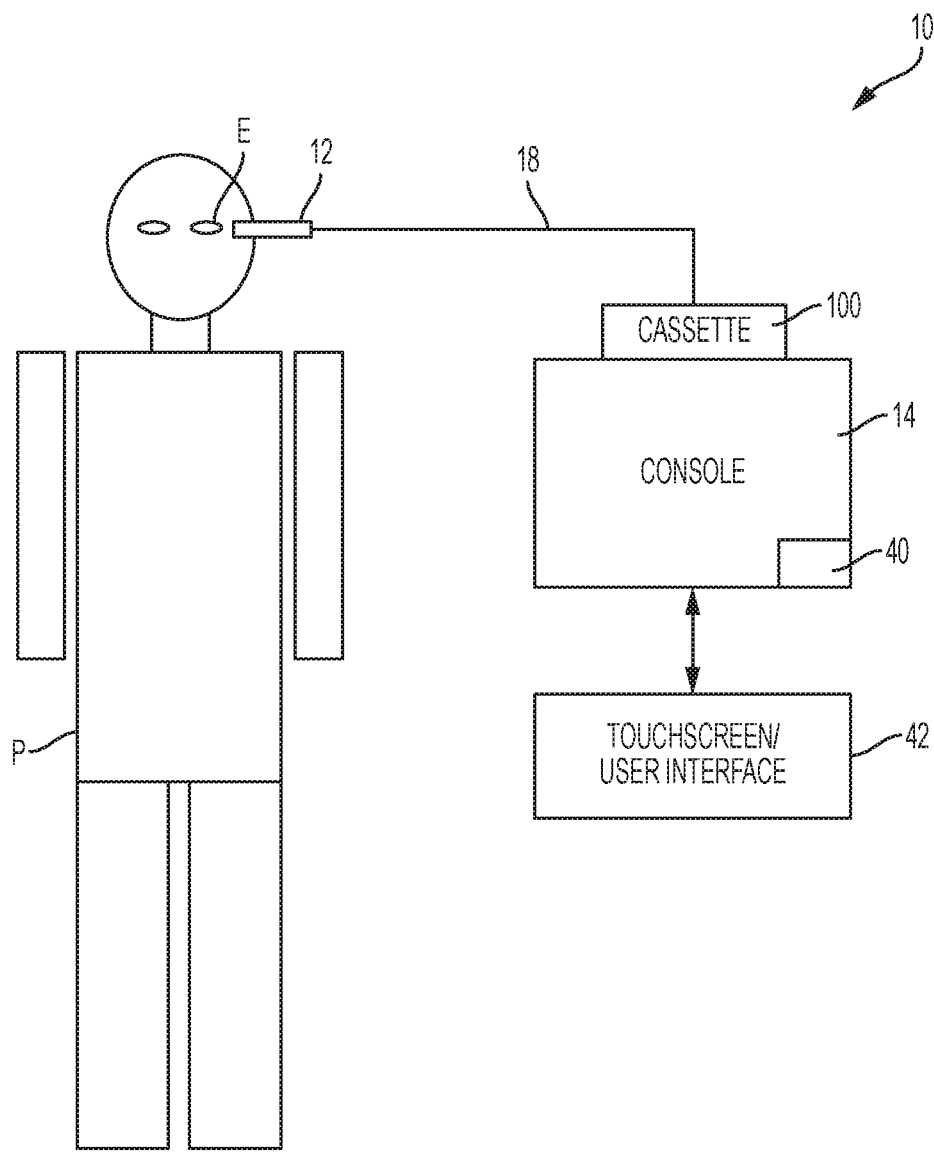
FIG. 1 schematically illustrates an eye treatment system in which a cassette couples an eye treatment probe with an eye treatment console.

Referring to FIG. 1, a system 10 for treating an eye E of a patient P generally includes an eye treatment probe handpiece 12 coupled to a console 14 by a cassette 100 mounted on the console. Handpiece 12 may include a handle for manually manipulating and supporting an insertable probe tip. The probe tip has a distal end which is insertable into the eye, with one or more lumens in the probe tip allowing irrigation fluid to flow from the console 14 and/or cassette 100 into the eye. Aspiration fluid may also be withdrawn through a lumen of the probe tip, with the console 14 and cassette 100 generally including a vacuum aspiration source, a positive displacement aspiration pump, or both to help withdraw and control a flow of surgical fluids into and out of eye E. As the surgical fluids may include biological materials that should not be transferred between patients, cassette 100 will often comprise a disposable (or alternatively, re-sterilizable) structure, with the surgical fluids being transmitted through flexible conduits 18 of the cassette that avoid direct contact in between those fluids and the components of console 14.

When a distal end of the probe tip of handpiece 12 is inserted into an eye E, for example, for removal of a lens of a patient with cataracts, an electrical conductor and/or pneumatic line (not shown) may supply energy from console 14 to an ultrasound transmitter of the handpiece, a cutter mechanism, or the like. Alternatively, the handpiece 12 may be configured as an irrigation/aspiration (FA) or vitrectomy handpiece. Also, the ultrasonic transmitter may be replaced by other means for emulsifying a lens, such as a high energy laser beam. The ultrasound energy from handpiece 12 helps to fragment the tissue of the lens, which can then be drawn into a port of the tip by aspiration flow. So as to balance the volume of material removed by the aspiration flow, an irrigation flow through handpiece 12 (or a separate probe structure) may also be provided, with both the aspiration and irrigations flows being controlled by console 14.

So as to avoid cross-contamination between patients without incurring excessive expenditures for each procedure, cassette 100 and its flexible conduit 18 may be disposable. Alternatively, the flexible conduit or tubing may be disposable, with the cassette body and/or other structures of the cassette being sterilizable. Regardless, the disposable components of the cassette are typically configured for use with a single patient, and may not be suitable for sterilization. The cassette will interface with reusable (and often quite expensive) components of console 14, which may include one or more peristaltic pump rollers, a Venturi or other vacuum source, a controller 40, and the like.

Controller 40 may include an embedded microcontroller and/or many of the components common to a personal computer, such as a processor, data bus, a memory, input and/or output devices (including a touch screen user interface 42), and the like. Controller 40 will often include both hardware and software, with the software typically comprising machine readable code or programming instructions for implementing one, some, or all of the methods described herein. The code may be embodied by a tangible media such as a memory, a magnetic recording media, an optical recording media, or the like. Controller 40 may have (or be coupled to) a recording media reader, or the code may be transmitted to controller 40 by a network connection such as an internet, an intranet, an Ethernet, a wireless network, or the like. Along with programming code, controller 40 may include stored data for implementing the methods described herein, and may generate and/or store data that records perimeters with corresponding to the treatment of one or more patients. Many components of console 14 may be found in or modified from known commercial phacoemulsification systems from Abbott Medical Optics Inc. of Santa Ana, Calif.; Alcon Manufacturing, Ltd. of Ft. Worth, Tex.; Bausch and Lomb of Rochester, N.Y.; and other suppliers.

Figure 2A:
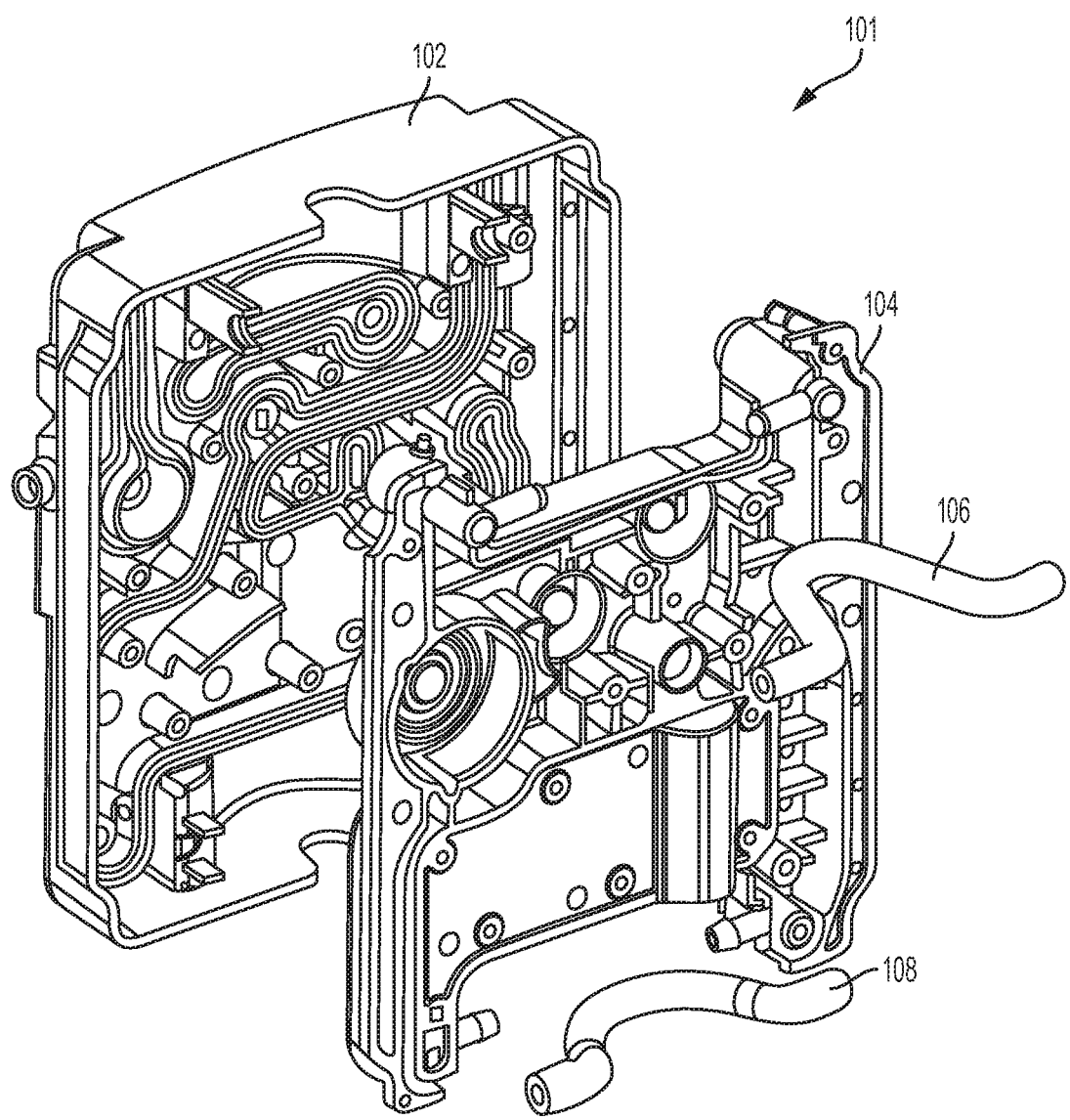
FIGS. 2A and 2B are exploded views of an exemplary surgical cassette manifold for use in the system of FIG. 1.
Figure 2B:
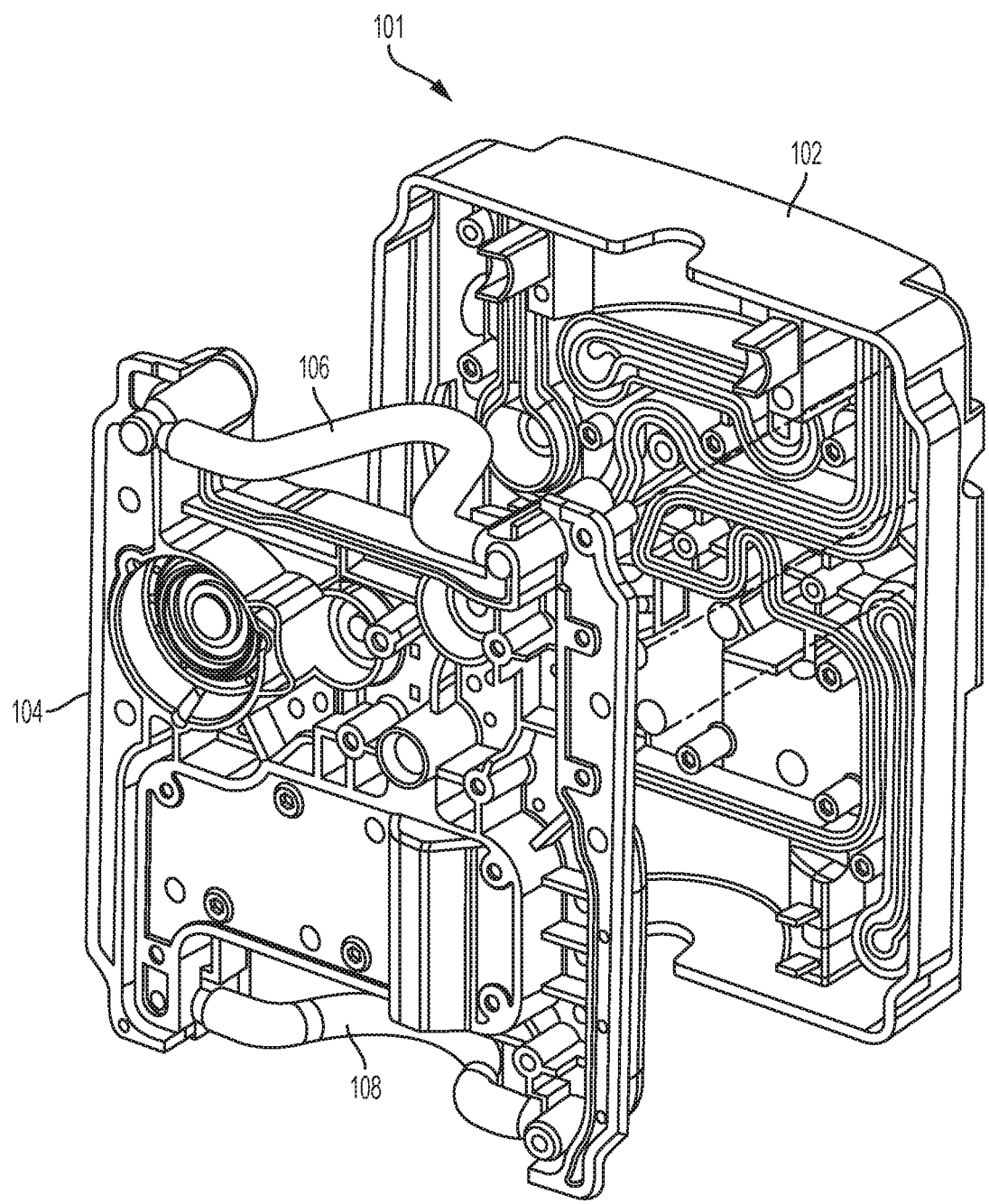

FIGS. 2A and 2B illustrates a surgical cassette manifold of the present invention, including components of surgical cassette manifold 101. Cassette or surgical cassette 100 is an assembly surgical cassette manifold 101 having fluid pathways and connected tubing configured to manage one or more of the following: fluid inflow, fluid outflow, fluid vacuum level, and fluid pressure in a patient's eye E when coupled with console 14. As shown in FIGS. 2A and 2B, surgical cassette manifold 100 has a front housing 102, a rear housing 104, a first tubing 106, and a second tubing 108. Rear housing 104 may also have gasket 110 co-molded or over-molded with rear housing 104.

Figure 3B:
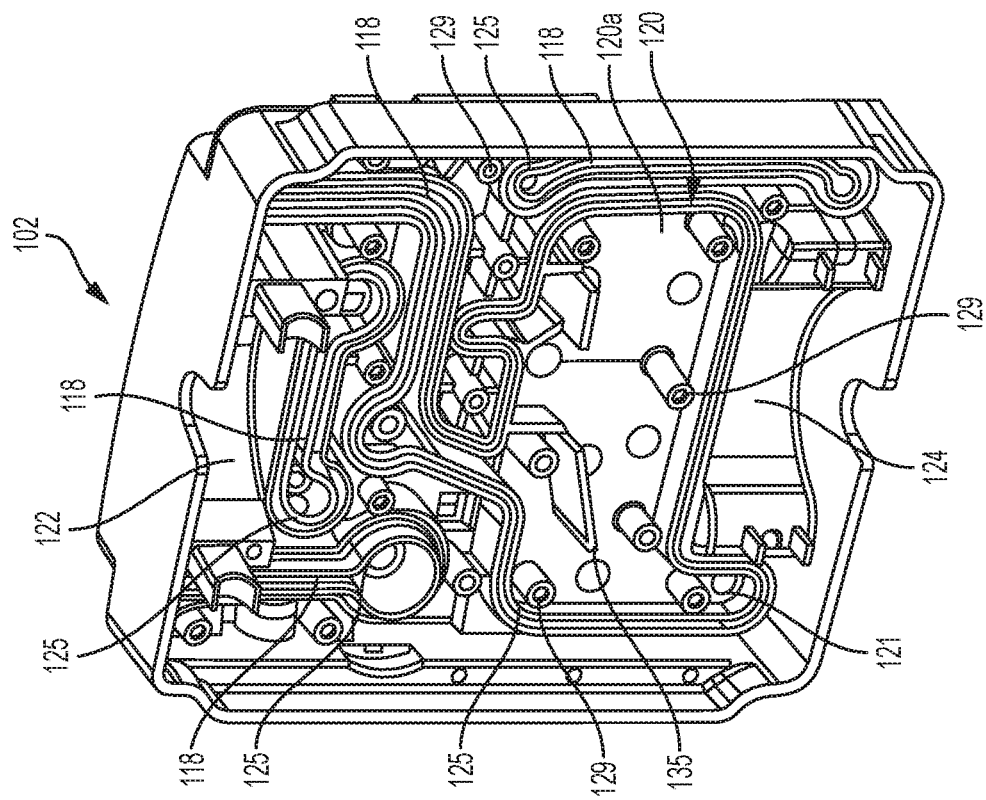
FIG. 3B is perspective back view of the front housing of an exemplary surgical cassette manifold.
Figure 3A:
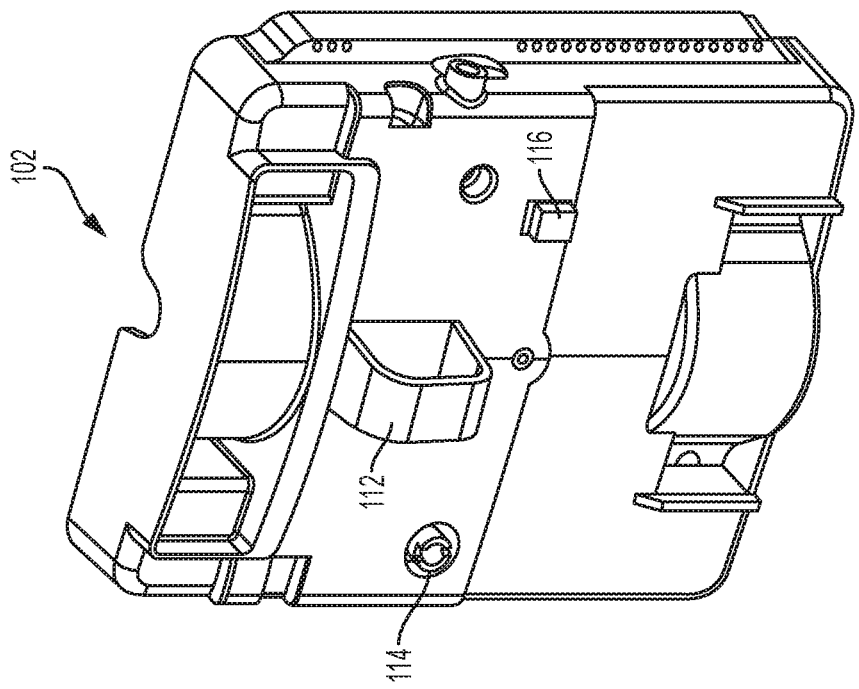
FIG. 3A is perspective front view of the front housing of an exemplary surgical cassette manifold.

FIGS. 3A and 3B show front housing 102 in more detail. FIG. 3A shows a front perspective view of front housing 102, which may have a handle 112 (e.g. finger grip handle), drain port 114, and attachment clip 116. FIG. 3B shows a back perspective view of front housing 102, which may have molded fluid channels 118, a first portion 120a of reservoir 120, a first pump ramp or profile 122 configured and dimensioned for mating with a peristaltic pump, and a second pump ramp or profile 124 configured and dimensioned for mating with a peristaltic pump.

Figure 6:
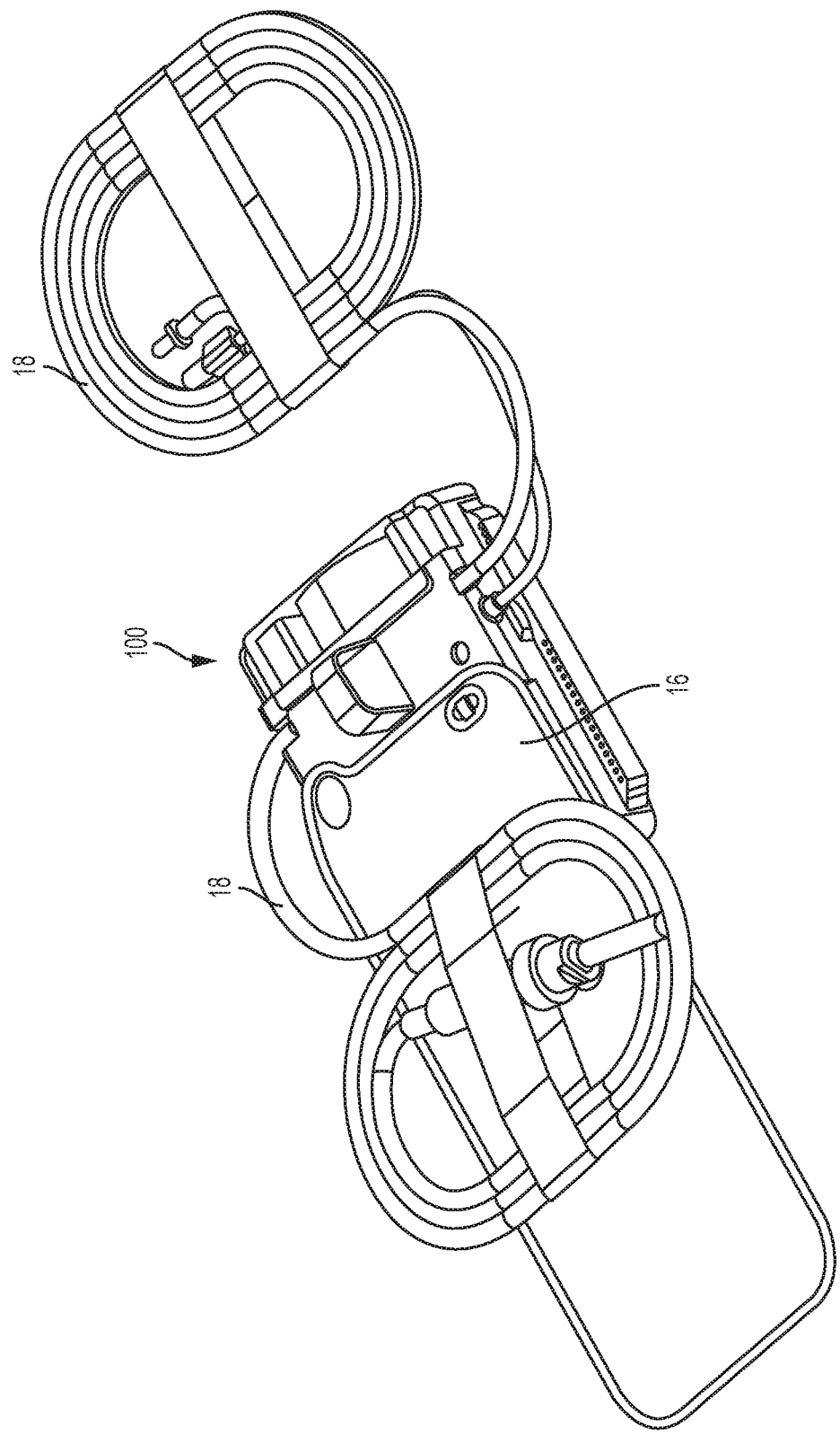
FIG. 6 is a perspective view of an exemplary surgical cassette with attached tubing and drain bag.

A drain bag 16 (see FIG. 6) may be attached to the front of front housing 102 via the drain port 114 and attachment clip 116 such that when surgical cassette 100 is coupled with console 14 and fluid is aspirated from an eye E of a patient P, the fluid is capable of being collected in the drainage bag 16 via drain port 114. The drain bag 16 may be supported on surgical cassette manifold 101 by attachment clip 116 and/or drain port 114.

Drain port 114 on front housing 102 of surgical cassette manifold 101 may be recessed allowing for a lower or low profile handle 112. Having a low or lower profile drain port 114 allows a drain bag (not shown) to sit flush again front housing 102. In an embodiment, placing drain port 114 substantially in the middle of the surgical cassette manifold from top to bottom moves the location of the center of mass of surgical cassette manifold 101 making the surgical cassette manifold more ergonomic. Moreover, locating drain port 114 closer to the upper/top edge of front housing 102 allows for a more compact assembly of the surgical cassette manifold and allows for better access to components/handles of console 14. See FIG. 6.

In an embodiment, a fluid channel 118 runs in a vertical direction from lower tube connection 136 (that is fluidly connected to the second tubing segment 108 that makes up the second peristaltic pump) to drain port 114 out to the drain bag 16. This molded fluid channel 118 eliminates the need for tubing.

As shown in FIG. 3B, front housing 102 also may have seal channels 125, which are configured and dimensioned to mate with a seal lip 126 (shown in FIGS. 4A, 4C, and 4E) that extends outwardly or perpendicularly from the surface of gasket 110 and is a part of gasket 110 to create a seal or lid over molded fluid channels 118. The seal lip may have any dimension suitable for mating with seal channel 125. In an embodiment, seal lip 126 may be tapered, starting thicker at its proximal end and becoming thinner towards its distal end. In another embodiment, seal lip 126 may be slightly larger than seal channel 125 to create a snug fit. In a further embodiment, co-molding or over-molding gasket 110 onto rear housing 104 eliminates the potential leak path in the direction of rear housing 104. Seal lip 126 provides positioning alignment on front housing 102 and rear housing 104.

Figure 4D:
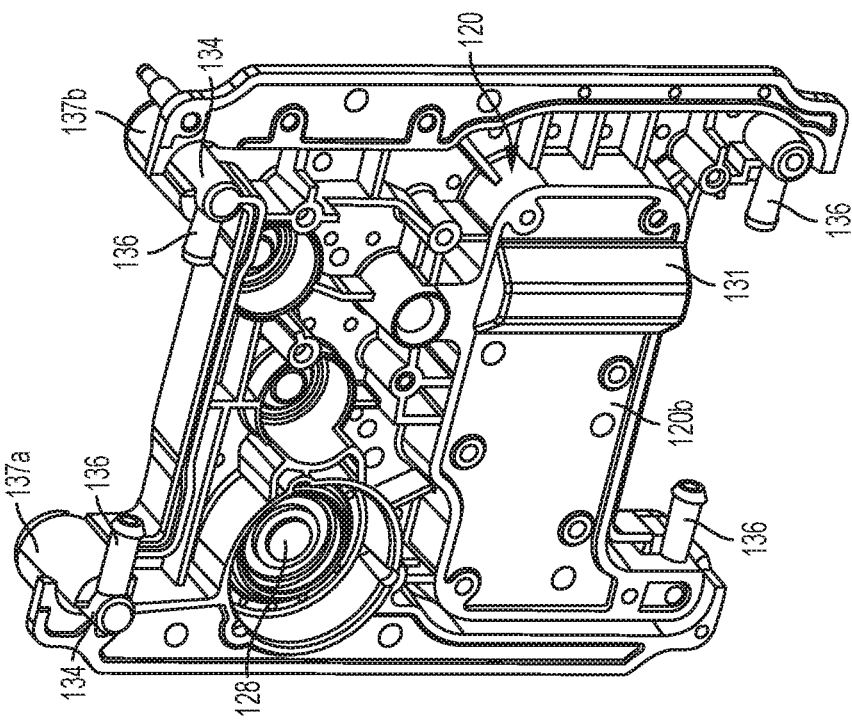
FIG. 4D is a back perspective view of the rear housing of an exemplary surgical cassette manifold.

Referring to FIGS. 4A-4F, various exemplary embodiments of rear housing 104 are shown. FIG. 4A is a front perspective view of rear housing 104 and FIG. 4B is a back perspective view of rear housing 104. As shown in FIG. 4A rear housing 104 has a gasket 110 co-molded or over-molded to it. Gasket 110 has seal lip 126 which extends away or protrudes in a substantially perpendicular direction from a plane of gasket 104 and rear housing 104. Gasket 110 may include a pressure/vacuum sensor diaphragm 128, vent valve control dome 130, and/or irrigation valve control dome 132. Vacuum/pressure sensor diaphragm 128 may be a sealed flexible annular membrane with a central magnetic coupling disk which deforms: (1) proportionally outwards under fluid pressure conditions compressing a magnetically-coupled force displacement transducer of console 14 allowing for non-fluid contact measurement of fluid pressure level inside the aspiration fluid pathways of surgical cassette manifold 101; and (2) proportionally inwards under fluid vacuum conditions extending the magnetically-coupled force displacement transducer of console 14 allowing for non-fluid contact measurement of fluid vacuum level inside the aspiration fluid pathways of surgical cassette manifold 101.

In an embodiment, gasket 110 may be molded, co-mold, or two-shot molded onto or with rear housing 104. Molding gasket 110 onto rear housing 104 in such a manner reduces or eliminates a leak path which is possible with molded fluid channels when using two different materials. In an embodiment, a method of eliminating leaking of molded fluid channels by combining two different materials for creating a proper seal is envisioned resulting in an easier manufacturing method by creating a self-aligning gasket 110. In an embodiment, when assembling rear housing 104 to front housing 102 mating of seal lip 126 and seal channel 125 can be achieved using a plurality of alignment pins 127 which mate with their counterpart pin holes 129. Using alignment pins 127 and pin holes 129 as opposed to the flexible seal lip 126 and seal channel 125 allows for an easier and more efficient assembly process. Thus, molding gasket 110 onto or with rear housing 104 results in pre-alignment/pre-keyed/pre-orientation of seal lip 126 for properly sealing molded fluid channels 118 on front housing 102, thus reducing or even eliminating leaking and increasing ease of manufacture.

Rear housing 104 may also include a second portion 120b of reservoir 120, upper tube connections 134, lower tube connection 136, and one or more tubing retainer clips 138. In an embodiment, upper tube connections 134 have a slight taper from bottom toward the top so that the tubing stays on the upper tube connections 134. See FIG. 5D. Lower tube connection 136 may have a tapered head (as shown in FIG. 5A) to secure second tubing 108 to lower tube connections 136.

In an embodiment, second tubing 108 may have a first end and a second end that couple with lower tube connections 136. Once surgical cassette manifold 101 is assembled, second tubing 108 and ramp 124 are configured to couple with a peristaltic rollers located on console 14 (not shown) to create a peristaltic pump. In an embodiment, lower tube connections 136 are on the same axis, i.e. there is axial alignment of the inflow and outflow of the tubing 108, and maintain a specific distance apart resulting in a more accurate peristaltic pump due to the controlled length of second tubing 106, which provides a consistent flow rate and a consistent interface with ramp 124 and peristaltic rollers. Moreover, such aligned and consistent interfaces results in less noise/sound generated by the peristaltic pump during operation.

In an embodiment, reservoir 120 may have a sump 121. Sump 121 is a portion of reservoir 120 that extends below a bottom 120c of reservoir 120 that promotes fluid to flow from the reservoir 120 to sump 121 and out a lower tube connection 136 via the second tubing 108. Sump 121 (1) reduces turbulence of the tank by pulling bubbles away from the level detector housed in the console 14 that couples with window 131 for more accurate detection of the fluid in reservoir 120; and (2) ensures drain inlet port 133a fluidly connected to a lower tube connection 136 is always below fluid, therefore fluid is consistently pumped out and not air, which may cause the drain bag 16 to balloon. In an embodiment, window 131 may be a prism.

In another embodiment, the fluid level detector and window 131 are located on one side of reservoir 120 and sump 121 and baffle 135 is on the other side of reservoir 120. This configuration ensures limited or no interaction between the fluid entering and exiting the reservoir and the fluid level detector and window 131 to allow for a more precise reading of the level of fluid in reservoir 120. Moreover, the combination of baffle 135 and sump 121 provides a guide for the fluid entering reservoir 120 from molded fluid channels 118 and exiting through drain pump inlet port 133a to reduce turbulence in reservoir 120. Fluid may exit reservoir 120 via drain pump inlet port 133a via lower tube connection 136, which may be coupled with a first end of second tubing 108 and a second end of second tubing 108 may be coupled to a second lower tube connection 136 which is coupled to drain pump outlet 133b. Drain pump outlet 133b is coupled with a drain bag 16 to allow fluid to be removed from reservoir 120 via the second peristaltic pump.

Figure 4C:
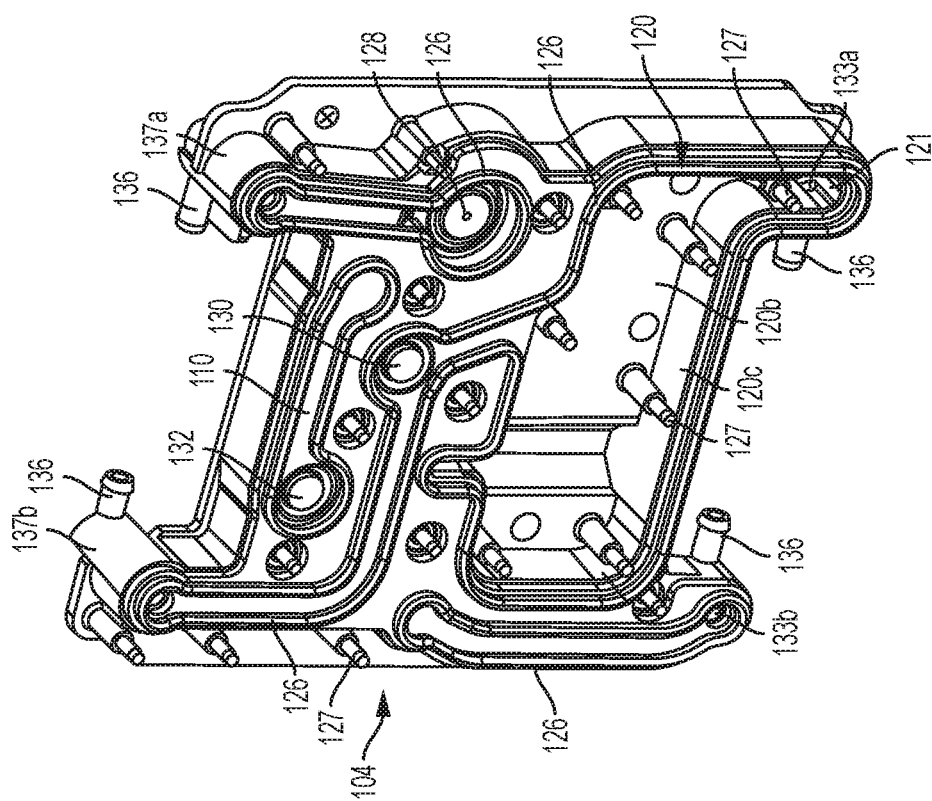
FIG. 4C is front perspective view of the rear housing of an exemplary surgical cassette manifold.

Referring to FIGS. 4C and 4D, rear housing 104 is shown in an alternative embodiment with respect to how first tubing 106 couples with rear housing 104. Pump tube inlet 137a and pump tube outlet 137b couple with barbs 136, which in turn are configured and dimensioned to couple with first tubing 106. See FIG. 2b. During assembly rear housing 104 is mated with front housing 102 and first tubing 106 is configured to conform with first pump ramp or profile 122, which is configured and dimensioned for mating with a peristaltic pump located within console 14 (not shown).

Figure 4F:
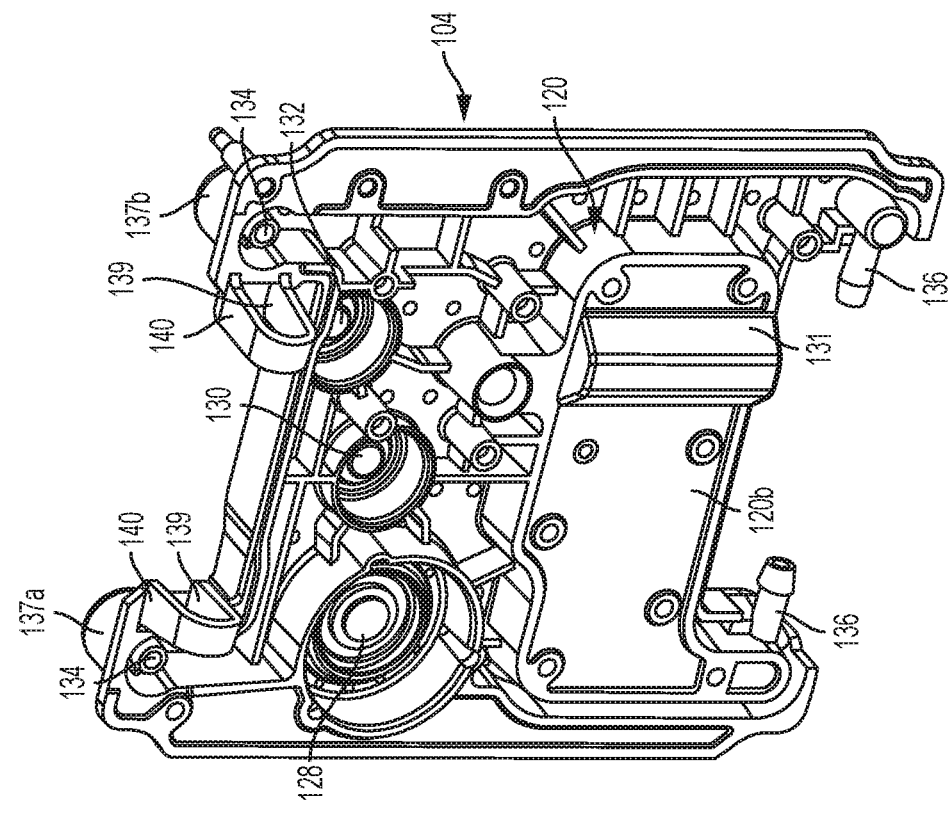
FIG. 4F is a back perspective view of the rear housing of an exemplary surgical cassette manifold.
Figure 4E:
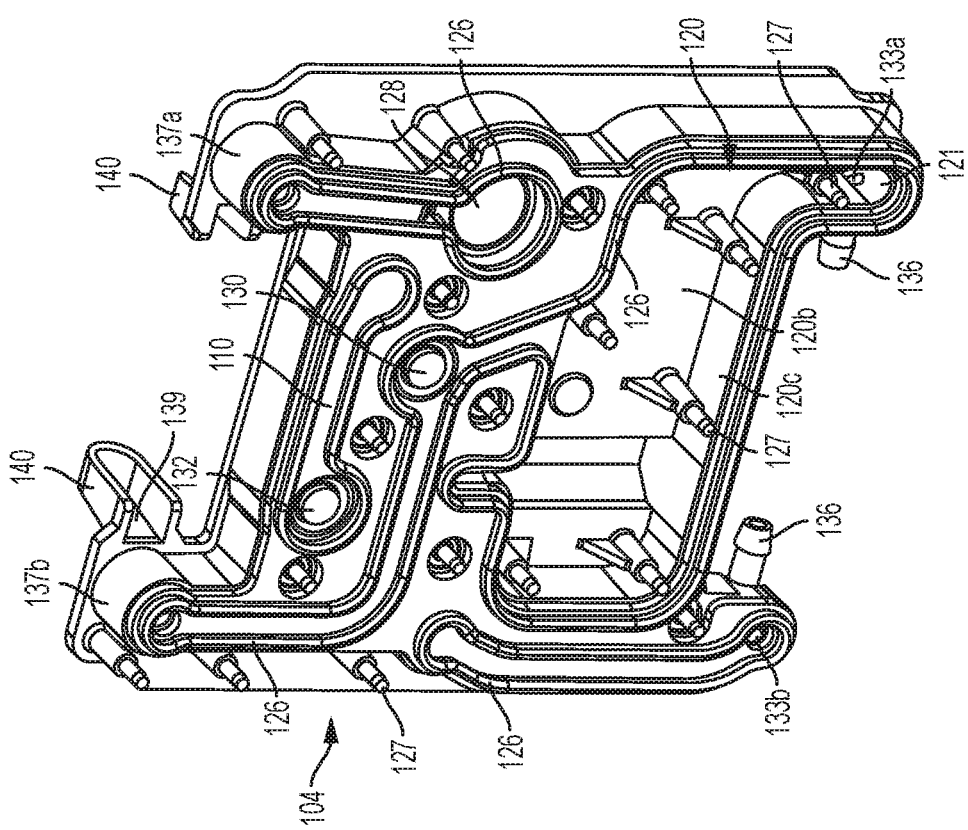
FIG. 4E is front perspective view of the rear housing of an exemplary surgical cassette manifold.
Figure 4G:
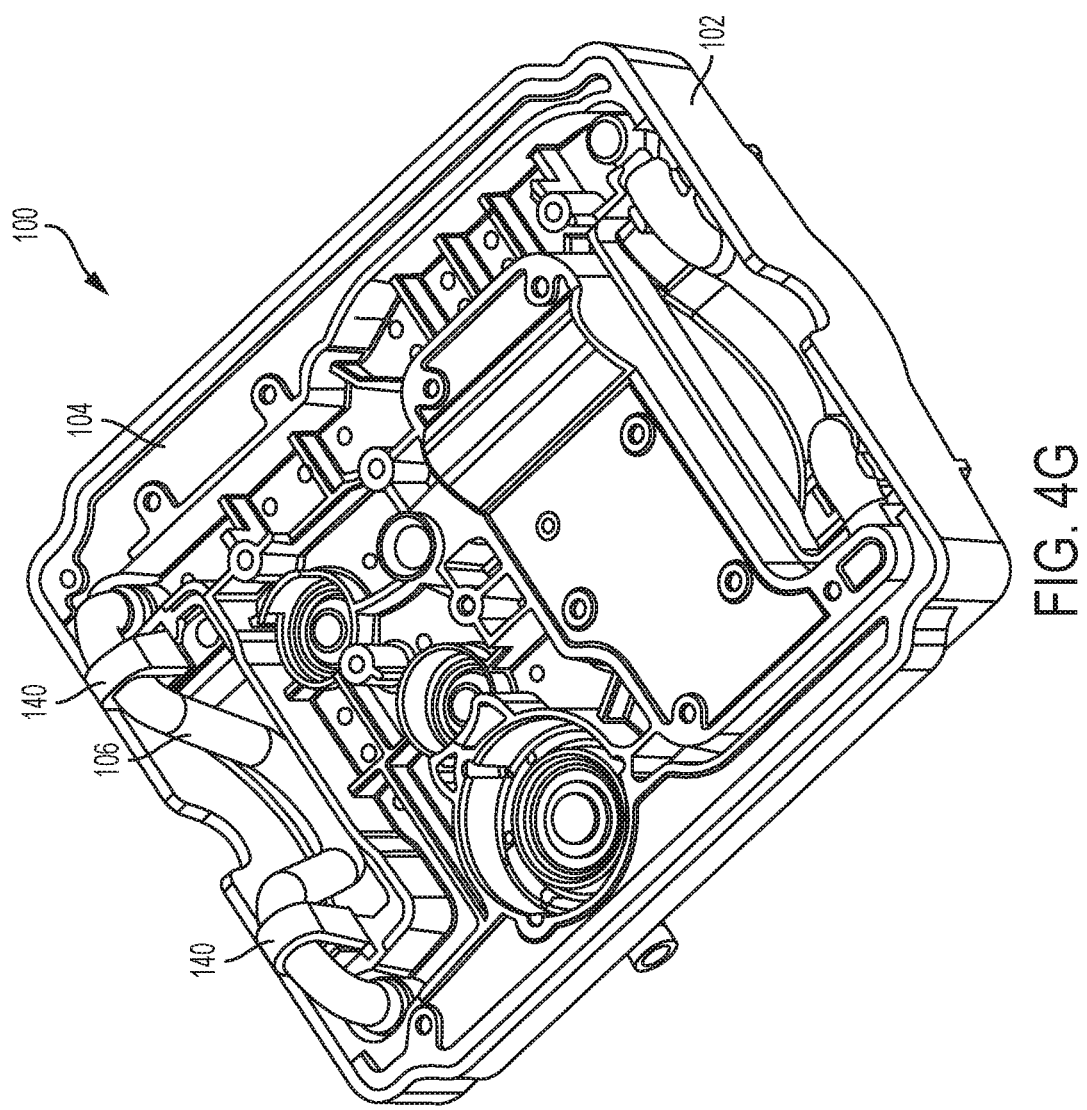
FIG. 4G is a back perspective view of an assembled exemplary surgical cassette having rear housing shown in FIGS. 4E and 4F.

Referring to FIGS. 4E and 4F, rear housing 104 is shown in an alternative embodiment with respect to how first tubing 106 couples with rear housing 104. A first end and a second end of first tubing 106 are fed through a gap 139 of tubing catch 140 and pump tube inlet 137a and pump tube outlet 137b couple with the first end and the second end of first tubing 106 via upper tube connections 134 by placing the first end and the second end of the first tubing 106 over the upper tube connection 134, which connect to molded fluid channels 118. Other mechanisms of connecting the first and second ends of first tubing 106 to upper tube connection 134 known in the art are also contemplated. FIG. 4G shows assembled cassette 100 having the rear housing 104 embodiment shown in FIGS. 4E and 4F with first tubing 106 fed through gaps 139 of tubing catch 140 of rear housing 104.

Referring to FIGS. 5A and 5B, tubing retainer clips 138 (shown in FIGS. 4A and 4B) may have a first prong 138a and a second prong 138b creating an opening 140. Tubing retainer clips 138 protrude substantially perpendicularly from a plane of the back side of rear housing 104. In an embodiment, tubing retainer clips 138 may slightly angle towards each other as shown in FIG. 5A. Tubing retainer clips 138 are configured and dimensioned to assist with easy assembly of surgical cassette manifold 101 and maintaining first tubing 106 in a specific orientation after assembly. Tubing retainer clips 138 may be over center clips.

During assembly of surgical cassette manifold 101, a first end and a second end of first tubing 106 are coupled with upper tube connections 134 (see FIG. 4B) via pump tube inlet 137a and pump tube outlet 137b by placing the first end and the second end of the first tubing 106 over the upper tube connection 134, which may connect to molded fluid channels 118. Once the first and second end of the first tubing 106 is coupled with the upper tube connections 134, first tubing 106 may be pushed through opening 140. First tubing 140 may pushed through opening 140 between the first prong 138a and the second prong 138b by an operators hand, using tool or through an automation step with equipment. The nature of the tubing allows for it to deform under pressure and fit between the first prong 138a and second prong 138b. In an embodiment, first tubing 106 may be stretched to minimize the diameter of the tubing to enable insertion between first prong 138a and second prong 138b. Once first tubing 106 is through first prong 138a and second prong 138b, the shape and size of first prong 138a, second prong 138b, and opening 140 prevent first tubing 106 from backing back out through opening 140 after assembly. In an embodiment, each prong has an angle to help with easing first tubing 106 into opening 140 and the angle between the first prong 138a and the second prong 138b is a as shown in FIG. 5B. In an embodiment, the angle between first prong 138a and second prong 138b may be approximately 60 degrees. In another embodiment, the larger the angle the easier to insert tubing 106 into opening 140, however a 0 degree angle would not help much. In an embodiment, the angle between first prong 138a and second prong 138b may be between 30 degrees and 90 degrees.

As discussed above and shown in FIGS. 3B and 4A, reservoir 120 may be comprised of two pieces with an elastomeric seal in between the two pieces. For example, reservoir 120 may include first portion 120a and second portion 120b. In prior art tanks that are composed of multiple pieces, adhesives are used resulting in additional material for assembly. In contrast, in an embodiment of the present invention, when front housing 102 and rear housing 104 are ultrasonically welded together with gasket 110 co-molded to the rear housing, gasket 110 creates a seal around and between the edges of the first portion 120a and the second portion 120 b. In the present embodiment, the joining of the first portion 120a and the second portion 120b with the co-molded or over-molded gasket 110 results in a mechanical seal. In another embodiment, the front housing 102 and rear housing 104 may be press fit together with or without the use of adhesives to replacing ultrasonic welding. These techniques may have a cost savings advantage of avoiding extra material from a manufacturing and cost of goods perspective. In another embodiment, other mechanisms of assembly that may be used to combine front housing 102 and rear housing 104 include, but are not limited to, laser welding, a rotating latch, a snap clip latch, or fasteners, such as screws, rivets, and/or pins.

According to an embodiment, having a first portion 102a and a second portion 102b with a gasket 110 decreases the dimensional tolerance requirements for the first and second portions where the gasket portion comes in contact with the reservoir 120 due to the compressive nature of the seal. In an embodiment, gasket 110 has a seal lip 126 that mates with a seal channel 125 on second portion 102b of the reservoir tank 120 of the rear housing 104, thereby creating a seal when the front housing 102 and rear housing 104 are mated. In an embodiment, there is no need to actually displace or squeeze the gasket between the two covers to create a non-leaking seal, although some pressure may be accommodated or desired, or may result from tolerances during manufacturing. See FIG. 3B.

Referring to FIGS. 5A and 5C, in an embodiment, rear housing 104 may have one or more venting/securing holes 142. The functionality of venting/securing holes 142 is two-fold. First, venting/securing holes 142 assist with venting or gas release during the co-molding or over-molding process when gasket 110 is coupled with rear housing 104. Holes 142 assist with the flow of material to minimize or eliminate the back pressure. Second, venting/securing holes 142 may be reversed tapered to help secure or increase adherence of gasket 110 to rear housing 104. For example, should the chemical reaction binding gasket 110 to rear housing 104 not occur or not completely occur, a mechanical adhesion can be achieved with the reversed taper of venting/securing holes 142. FIG. 5C shows a cross-section along J-J showing holes 142. Holes 142 may have any degree of taper suitable for securing gasket 110 to rear housing 104 and/or making molding/manufacturing easier.

In an embodiment, surgical cassette manifold 101 may be made substantially of a plastic material except for gasket 110. The plastic material may be acrylonitrile-butadiene-styrene (ABS), polycarbonate (PC), polyethylene, viton, or other rigid plastic or plastic material. In addition, the material may be such that it is transparent enabling a user to visualize various features of surgical cassette manifold 101. For example, all components may be transparent, including reservoir 120. In an embodiment, a lights emitted from console 14 may be shone through surgical cassette manifold 101 to provide a backlight and allow a user to visualize the fluid flow as it flows from handpiece 12 through molded fluid channels 118 into reservoir 120 out to the drain bag 16. In embodiment, the backlight may also be used as a surgical cassette manifold type detector.

All references cited herein are hereby incorporated by reference in their entirety including any references cited therein.

Although the present invention has been described in terms of specific embodiments, changes and modifications can be carried out without departing from the scope of the invention which is intended to be limited only by the scope of the claims.

The invention claimed is:

1. A surgical cassette manifold, comprising:
   a reservoir,
      wherein the reservoir comprises a sump and a baffle,
   wherein a port for fluid outflow is located within the sump;
   a front housing,
      wherein the front housing has a first side and a second side,
      wherein the first side comprises one or more fluid channels and a first half of the reservoir; and
   a rear housing,
      wherein the rear housing has a first side and a second side,
      wherein the first side comprises a second half of the reservoir and a gasket molded to at least a portion of the first side,
      wherein the first half of the reservoir comprises a baffle located near a top of the reservoir;
   wherein the sump is configured and dimensioned to draw fluid to the port to reduce turbulence in the reservoir.

2. The cassette of claim 1, further comprising a fluid level window, wherein the baffle is configured and dimensioned to limit fluid contact with the fluid level window.

3. The cassette of claim 1, wherein the baffle is angled toward the sump to direct fluid flow from the fluid channels to the port.

* * * * *